United States Patent
Yang-Woytowitz et al.

(10) Patent No.: US 11,845,919 B2
(45) Date of Patent: Dec. 19, 2023

(54) BLOOD CULTURE SYSTEM WITH LOW MEDIA VOLUME

(71) Applicant: BECTON, DICKINSON AND COMPANY, Franklin Lakes, NJ (US)

(72) Inventors: Mei Yang-Woytowitz, Baltimore, MD (US); Song Shi, Reisterstown, MD (US); Xiaofei Chang, Timonium, MD (US); James Y. Zhou, Columbia, MD (US); Michael A. Brasch, Gaithersburg, MD (US)

(73) Assignee: BECTON, DICKINSON AND COMPANY, Franklin Lakes, NJ (US)

(*) Notice: Subject to any disclaimer, the term of this patent is extended or adjusted under 35 U.S.C. 154(b) by 247 days.

(21) Appl. No.: 15/573,266

(22) PCT Filed: May 13, 2016

(86) PCT No.: PCT/US2016/032341
§ 371 (c)(1),
(2) Date: Nov. 10, 2017

(87) PCT Pub. No.: WO2016/183434
PCT Pub. Date: Nov. 17, 2016

(65) Prior Publication Data
US 2019/0078043 A1    Mar. 14, 2019

Related U.S. Application Data

(60) Provisional application No. 62/161,380, filed on May 14, 2015.

(51) Int. Cl.
| | | |
|---|---|---|
| *C12M 1/24* | (2006.01) | |
| *C12M 1/34* | (2006.01) | |
| *C12N 5/078* | (2010.01) | |
| *C12M 1/00* | (2006.01) | |

(52) U.S. Cl.
CPC ............ *C12M 23/08* (2013.01); *C12M 23/00* (2013.01); *C12M 41/46* (2013.01); *C12N 5/0634* (2013.01); *C12N 2501/999* (2013.01)

(58) Field of Classification Search
None
See application file for complete search history.

(56) References Cited

U.S. PATENT DOCUMENTS

| | | | |
|---|---|---|---|
| 6,410,334 B1 | 6/2002 | Schmolz | |
| 6,432,697 B1* | 8/2002 | Tice | C12M 23/08 356/246 |
| 2011/0029249 A1 | 2/2011 | Beaty | |

FOREIGN PATENT DOCUMENTS

| | | |
|---|---|---|
| WO | 2014039498 A1 | 3/2014 |

OTHER PUBLICATIONS

BD BACTEC Myco/F Lytic Vials, Product Information, 2016: retrieved from the internet Jan. 25, 2020: http://legacy.bd.com/ds/technicalCenter/inserts/PP162JAA(05).pdf (Year: 2016).*
BD BACTEC™ Standard/10 Aerobic/F Culture Vials, Product Information, 7 pages; retrieved from the internet Mar. 22, 2021: https://www.bd.com/resource.aspx?IDX=18396 (Year: 2021).*
Linoj P. SAMUEL et al. "Comparison of time to positivity of the VersaTREK® REDOX 80-mL and the REDOX EZ draw 40-mL blood culture bottles for common bacterial bloodstream pathogens", SciVerse ScienceDirect , 2011, pp. 6.
Extended European Search Report issued in corresponding EP application No. 16793603.8 dated Dec. 5, 2018, pp. 7.
International Search Report from PCT Application No. PCT/US2016/032341 dated Aug. 19, 2016.
Forbes, B., et al., "Diagnostics Microbiology", Part 3: Diagnosis by Organ System, 10th ed., (1998), p. 292.
Lee, Andrew, et al., "Detection of Bloodstream Infections in Adults: How Many Blood Cultures are Needed?", Journal of Clinical Microbiology, vol. 45, No. 11, (2007), pp. 3546-3548.
Patel, Robin, et al., "Optimized Pathogen Detection with 30- Compared to 20-Milliliter Blood Culture Draws", Journal of Clinical Microbiology, vol. 49, No. 12, (2011), pp. 4047-4051.
Versalovic, J., et al., "Manual of Clinical Microbiology", vol. 1, Diagnostic Strategies and General Topics, 10th ed., ASM Press, (Murray, P.R. et al., eds.), (2003), p. 16.
Weinstein, Melvin P., "Current Blood Culture Methods and Systems: Clinical Concepts, Technology, and Interpretation of Results", Clinical Infectious Diseases, vol. 23, No. 1, (1996), pp. 40-46.
Wilson, Michael L., et al., "Principles and Procedures for Blood Cultures; Approved Guidelines,", Clinical and Laboratory Standards Institute, M47-A, vol. 27, No. 17, (May 2007), p. 8.
Office Action from Japanese Patent Application No. 2017-559540 dated Mar. 3, 2020 (4 pages).
Decision of Rejection issued in corresponding Japanese Patent Application No. 2017-559540 dated Jan. 21, 2021.
Office Action issued in corresponding Japanese Patent Application No. 2017-559540 dated Mar. 10, 2022, 11 pp.
Alberts, B. , et al., "Fractionation of Cells", Alberts B, Johnson A, Lewis J, et al. Molecular Biology of the Cell. 4th edition. New York: Garland Science; 2002. Fractionation of Cells. Available from: https://www.ncbi.nlm.nih.gov/books/NBK26936/, 2002, 11 pp.

(Continued)

*Primary Examiner* — Allison M Fox
*Assistant Examiner* — Alyssa G Weston
(74) *Attorney, Agent, or Firm* — Botos Churchill IP Law LLP (57) ABSTRACT

A container for culturing a blood sample. The container has a reservoir that is no larger than about 40 ml in volume with culture media therein varying in amount by volume 0.5 ml to about 20 ml. The container is adapted to receive a blood sample drawn from a patient, wherein the blood volume is about 1 ml to about 20 ml. In some embodiments the ratio of blood volume to culture media volume is about 2:1 to about 1:2 and the volume of blood does not exceed about 10 ml. In some embodiments, the media is lytic media. A method for using the container to culture a blood sample is also contemplated. In such method, the container is inoculated with the blood sample. In certain embodiments, the volume of the blood sample does not exceed 10 mls.

5 Claims, 4 Drawing Sheets

(56) References Cited

OTHER PUBLICATIONS

Bennett, A., et al., "Microbial aerosol generation during laboratory accidents and subsequent risk assesment", Bennett A, Parks S. Microbial aerosol generation during laboratory accidents and subsequent risk assessment. J Appl Microbiol. Apr. 2006;100(4):658-63. doi: 10.1111/j.1365-2672.2005.02798.x. PMID: 16553720., 2006, pp. 658-653.
Buxton, Rebecca, "Blood Agar Plates and Heolysis Protocols", Buxton, R., Blood Agar Plated and Hemolysis Protocols, American Society for Microbiology, 2016, pp. 1-9.
Peterson, Brandon W., et al., "Bacterial Cell Surface Damage Due to Centrifugal Compaction", Peterson BW, Sharma PK, van der Mei HC, Busscher HJ. Bacterial cell surface damage due to centrifugal compaction. Appl Environ Microbiol. Jan. 2012;78(1):120-5. doi: 10.1128/AEM.06780-11. Epub Oct. 28, 2011. PMID: 22038609; PMCID: PMC3255633., Jan. 2012, pp. 120-125.
Office Action issued in corresponding Japanese Patent Application No. 2017-55954 dated Oct. 25, 2022 (18 pp.).
Office Action from corresponding Japanese Application No. 2017-55954 dated Oct. 25, 2022 (18 pp.).

\* cited by examiner

FIG. 3C
CONTROL

FIG. 3B
REGULAR RATIO (1:4) PlusLytic

FIG. 3A
LOW VOLUME/LOW RATIO

Plus Aer
1:4 RATIO (NO LYTIC MEDIA, BUT WITH RESIN)

| | | PLUS AER (CONTROL) | | |
|---|---|---|---|---|
| | | NEGATIVE | POSITIVE | TOTAL |
| LowVol | NEGATIVE | 15 | 2 | 17 |
| | POSITIVE | 6 | 41 | 47 |
| | TOTAL | 21 | 43 | 64 |

FIG. 4A

PlusLytic
1:4 RATIO (WITH LYTIC)

| | | PLUS AER (CONTROL) | | |
|---|---|---|---|---|
| | | NEGATIVE | POSITIVE | TOTAL |
| PlusLytic | NEGATIVE | 16 | 1 | 17 |
| | POSITIVE | 5 | 42 | 47 |
| | TOTAL | 21 | 43 | 64 |

FIG. 4B

LOW VOLUME/LOW RATIO
1:1 RATIO

| | | PLUS LYTIC | | |
|---|---|---|---|---|
| | | NEGATIVE | POSITIVE | TOTAL |
| LowVol | NEGATIVE | 15 | 2 | 17 |
| | POSITIVE | 2 | 45 | 47 |
| | TOTAL | 17 | 47 | 64 |

FIG. 4C

BLOOD CULTURE SYSTEM WITH LOW MEDIA VOLUME

CROSS-REFERENCE TO RELATED APPLICATION

The present application is a national phase entry under 35 U.S.C. § 371 of International Application No. PCT/US2016/032341 filed May 13, 2016 published in English, which claims priority from U.S. Provisional Application No. 62/161,380 filed May 14, 2015, all of which are incorporated herein by reference.

BACKGROUND OF THE INVENTION

Sepsis is a significant healthcare issue due to its high frequency of occurrence and high mortality rate in hospitals. One of the leading causes of sepsis is a bloodstream infection (BSI). BSI is most commonly diagnosed by a blood culture, in which a sample of blood is incubated with a microorganism growth media in an atmosphere controlled closed system to promote bacterial growth. Current automated blood culture systems can take 12-48 hours to detect the presence of infectious microorganisms in blood and can take up to 5 days to rule out the presence of any infectious microorganisms.

Often times, additional substances must be combined with the blood culture to ensure that the presence or absence of a BSI is determined as quickly and accurately as possible. For example, a patient's blood at the time of sampling may already contain antibiotics. The presence of antibiotics can further increase the time required to detect the presence of infectious microorganisms. Furthermore, it can take up to an additional 12-48 hours to identify the microorganisms causing the infection by sub-culturing the positive blood culture and performing identification and antimicrobial susceptibility tests. These results can be too late to alter the treatment course and result in more serious illness and even in the death of the patient. Therefore, additives that adsorb the antibiotics and neutralize their inhibitory effect on microbial growth are also added to blood culture media.

The current blood culture systems have broth mixtures of various reagents that promote microorganism growth and a faster time to detection. One important factor to promote microorganism growth is to dilute the blood samples with growth media. Diluting patient's blood with growth media is believed to reduce the inhibitory effect of antibiotics and the patient's immune response components that may be present in the blood sample.

Adsorption resins of various kinds can be used to adsorb antibiotics in a patient's blood sample in order to be able to recover the microorganisms, improve the recovery of the microorganisms and/or reduce the time required to detect the microorganism growth at high antibiotic concentrations that inhibit microorganism growth. Adsorption resins, nevertheless, can also adsorb other constituents of the media that are essential for early detection of microorganism growth. When the media is a lytic media, the adsorption resin may adsorb components of the lytic reagent (e.g., saponin). Such adsorption causes a reduction in both lytic function and nutrients essential for microorganism growth, resulting in a longer time to detection.

The recommended blood-to-broth ratio is in the range from about 1:5 to about 1:10 in order to reduce or minimize or control the inhibitory effect of substances like antibodies and antibiotics. See Wilson, Michael L., et al., *Principles and Procedures for Blood Cultures; Approved Guidelines*, Clinical and Laboratory Standards Institute, M47-A, Vol. 27, No. 17, p. 8 (May 2007) and Versalovic, J., et al., *Manual of Clinical Microbiology*, Vol. 1, Diagnostic Strategies and General Topics, p. 16, 10th ed., ASM Press, (2003)(Murray, P. R. et al., eds.). The accepted preference is for larger volumes of blood sample (10 ml to 20 ml per draw) for culture. See Forbes, B., et al. *Diagnostics Microbiology*, Part 3: Diagnosis by Organ System ($10^{th}$ ed. 1998). P 292.

The recommended blood volume used to inoculate the blood culture bottle is about 8 ml to about 10 ml, making the recommended broth volume between at least 50 and 150 ml. Thus, the containers used for this kind of blood culture are bulky, making it difficult to precisely control the volume of the blood draw to precisely draw the specified 8-10 ml of blood volume of 8-10 ml blood (Weinstein, Melvin P. *Current Blood Culture Methods and Systems: Clinical Concepts, Technology, and Interpretation of Results*. The University of Chicago, Clinical Infectious Diseases, 1996). In addition, there are also economic, ergonomic and environmental needs to shrink the blood culture consumable.

With the improvement of media components, especially incorporation of resin into growth media, the broth volume needed for microbial growth can be reduced because the resin will adsorb some of the antibiotics, if present, mitigating the adverse effects of the antibiotics on microbial growth. Thus, current blood culture systems have been successful with 1:3 and 1:4 blood to broth volume ratios. One example is the Becton BACTEC™ (a trademark of Becton Dickinson and Company) Plus Aerobic product, which uses at least a 1:3 blood-to-broth ratio with an 8-10 ml blood volume sample. It is still the current belief that high concentrations of blood-to-broth ratios (e.g. 1:2 and greater) are not effective in producing the necessary amount of overall positive cultures needed for detection and should be avoided. (Weinstein, *Current Blood Culture Methods and Systems*). However, despite improvements in efficacy achieved through the use of resins, blood culture environments that provide gains in time to detection while reducing the amount of blood sample and/or broth required continue to be sought.

BRIEF SUMMARY OF THE INVENTION

According to one embodiment of the present invention, a blood sample is delivered into a culture media such that the blood volume is in the range of about 4 ml to about 10 ml and the ratio of the blood volume to the volume of the culture media into which the blood sample is delivered is about 2:1 to about 1:2. In certain embodiments the ratio is about 1:1. The range of culture media volumes is therefore about 2 ml to about 20 ml in the embodiments where the blood-to-media ratio is about 2:1 to about 1:2. In the embodiments where the blood-to-media ratio is about 1:1, the volume of the media is about 4 ml to about 10 ml.

According to another embodiment of the present invention, the blood volume is about 1 ml to about 3 ml, in which embodiment the volume of culture media is in the range of about 0.5 ml to about 6 ml.

In another embodiment of the present invention, the volume of culture media is less than 40 ml and the ratio of blood volume to culture media is in the range of about 2:1 to about 1:2 wherein the blood volume does not exceed about 20 ml.

According to another embodiment of the present invention, the blood volume is about 3 ml to about 4 ml and the ratio of blood volume to volume of culture media is about 2:1 to about 1:2.

DETAILED DESCRIPTION

Described herein are methods for preparing and testing blood culture samples in higher concentration of blood in broth (providing lowered blood-to-broth ratios). Preferably, "higher concentration of blood in broth" refers to a broth (or media) volume that is equal to or less than the blood volume of a culture sample (e.g. 1:1, 2:1). Media and broth are used interchangeably herein. Samples with higher concentrations of blood in broth (i.e. providing lower blood-to-broth ratios) described herein showed similar or even improved time-to-detection ("TTD") results as compared with current industry blood culture sample bottles that use a more diluted blood-to-broth ratio (e.g. 1:3, 1:4). As used herein, time-to-detection or "TTD" is defined as the time elapsed between the time point that blood microorganisms are inoculated into the containers and the time point that the system can detect microorganism growth in the containers.

In one embodiment, the blood cultures do not contain antibiotic inhibitors. In another embodiment, the blood cultures contain a predetermined amount of antibiotic inhibitor.

Figure 1:
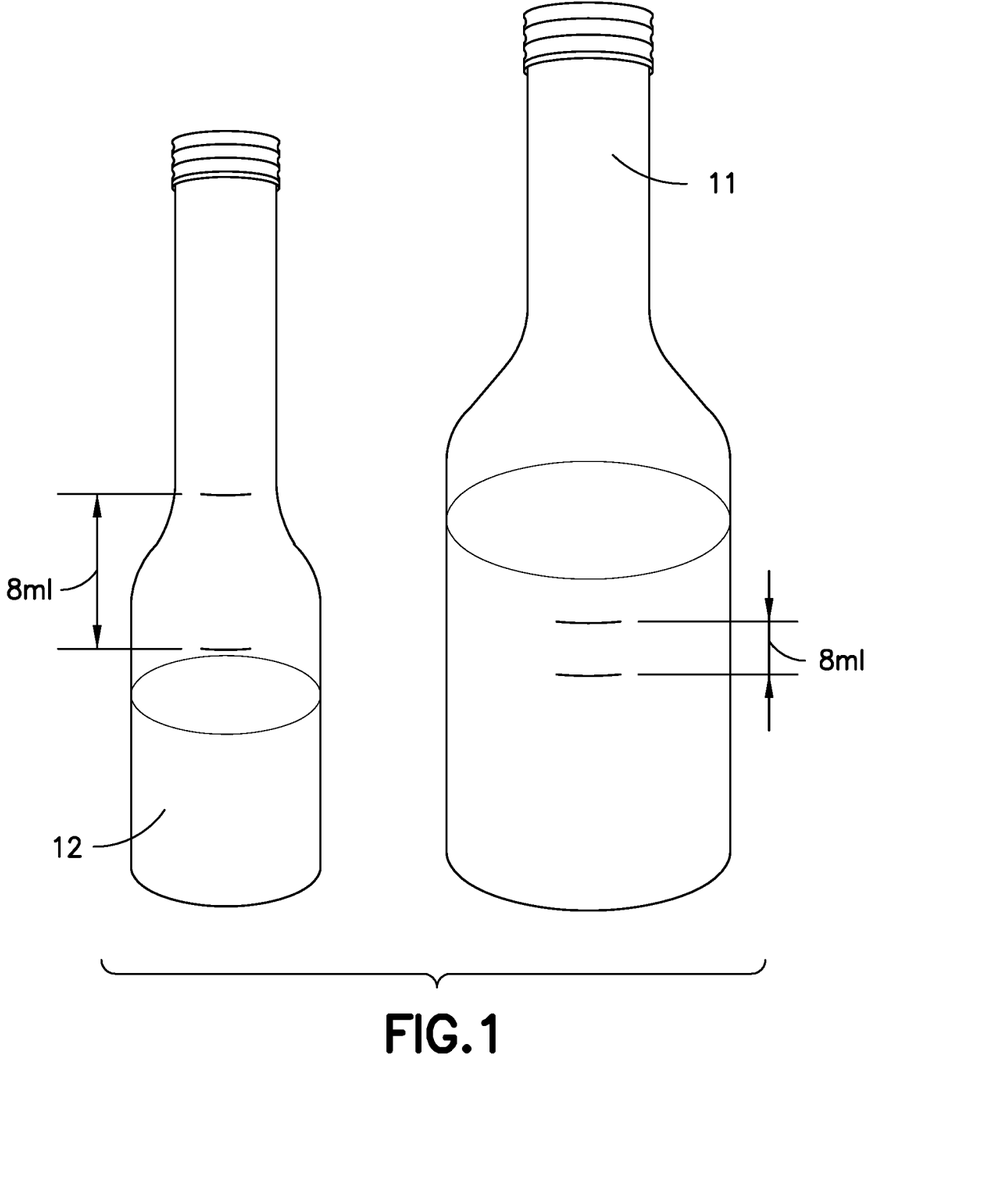
FIG. 1 illustrates two different configurations of a blood culture bottle for use in an embodiment of the present invention.

The methods described herein use blood cultures having lower blood-to-broth ratios, of 1:1 up to about 2:1. The volume and configuration of blood culture bottles in which the blood cultures are disposed may vary. For example, FIG. 1 illustrates two different configurations of a blood culture bottles. Bottle 11 is an 80 ml bottle currently sold as BACTEC™ Plus Aerobic bottle which is 80 ml bottle that contains 30 ml liquid culture media and resin in the range of about 2 grams to about 6 grams. BACTEC™ is a trademark of Becton Dickinson and Company. The bottle 12 is a 30 ml bottle provided with about 8 ml of culture media and resin also in the range of about 2 grams to about 6 grams. The media volume can vary is in the range of about 5 ml to about 20 ml. The actual volume of the bottle is largely a matter of design choice depending on such factors as bottle volume, configuration of head space, total volume of blood and broth to be received by the bottle, sensor type, sensor configuration, etc. Alternative bottle or vessel configurations include test tubes, cylinders, flasks, etc.

Using a lower blood-to-broth ratio allows for a smaller amount of growth media and reagents, allowing smaller volume blood culture bottles to be used. Smaller volume blood culture bottles may have a reduced diameter, a shorter height, or both. The reduced diameter bottles also allows for a more accurate amount of blood draw by indicating volume more precisely than the larger 80 ml. bottle. The reduction in volume also reduces the cost of the consumable and allows a reduction in the instrument footprint by permitting more vials to be tested at once compared to the current standard 80 ml bottles.

Example 1: Comparison of Time to Detection (TTD) for Various Microorganisms Using Standard Ratio/Standard Volume and Low Ratio/Low Volume Time to Detection was compared for the standard ratio of about 1:5 blood to media volume (i.e. 8 ml of blood and 40 ml of culture media) with 1:1 blood to media volume. Both media with no lysis reagent (non-lytic media) and media with a lysis regent (lytic media) were used. The non-lytic media was the BACTEC™ Aerobic Media. For the 1:4 ratio samples, 40 ml of media was used. The standard BACTEC Aerobic bottles contain 40 ml of media. So for the 1:1 ratio examples, 32 ml of media were removed from the bottle before the sample was introduced into the bottle. To make the media lytic, about 0.25% of saponin was added to the media.

As noted above, four sets of samples were prepared. Two sets had the 1:4 standard blood-to-broth ratio and two sets had the 1:1 ratio. One of the two sets for each ratio had non lytic media and the other set had lytic media. To create the samples with the 1:1 blood-to-broth ratio, 32 mls of the 40 mls of media in the standard BACTEC Aerobic bottle was withdrawn, leaving only 8 ml broth remaining. To make the broth lytic, a lytic reagent, saponin, was added to the remaining broth (40 mls for the 1:4 ratio and 8 mls for the 1:1 ratio) in an amount to yield a concentration of 0.25% in the respective standard ratio and low ratio samples. About 8 ml of blood and 10-100 cfu of each of the microorganism listed in Table 1 below were inoculated into each of the bottles. The BACTEC Standard Aerobic bottles with the original 40 ml media was used for those samples having the 1:4 blood to broth ratio. All inoculated bottles were placed into the BD BACTEC™ FX instrument and cultured for 5 days at 35° C. The result showed that the time to detection for the eight microorganisms identified in Table 1 below were comparable with each other. Therefore, the 1:1 blood to media ratio supports microorganism growth in blood culture even though the blood dilution factor for the low 1:1 ratio was significantly less than the conventional 1:4.

TABLE 1

TTD for Various Organisms Using Standard Ratios and Volumes and Low Ratios and Volumes

| | TTD (hrs) | | | |
|---|---|---|---|---|
| Organisms | 1:4 BMR non lytic | 1:4 BMR lytic | 1:1 BMR non lytic | 1:1 BMR Lytic |
| Acinetobacter lwoffii | 15.0 | 15.2 | 14.6 | 21.1 |
| Candida albicans | 25.8 | 26.6 | 27.0 | 28.3 |
| Candida glabrata | 64.0 | 50.0 | 70.0 | 68.0 |
| Cryptococcus neoformans | 75.0 | 80.0 | 80.0 | 65.0 |
| Escherichia coli | 10.9 | 10.7 | 10.7 | 10.4 |
| Pseudomonas aeruginosa | 15.1 | 14.9 | 16.7 | 15.5 |
| Staphylococcus aureus | 12.5 | 11.8 | 13.6 | 11.4 |
| Streptococcus pneumoniae | 14.5 | 19.1 | 14.1 | 14.7 |

Surprisingly, the samples with the 1:1 ratio (low ratio/low volume) performed similarly to the samples with the 1:4 ratio (standard ratio/standard volume). Also, the above table shows that, for some microorganisms, the TTD was lower for the bottles with the lytic media than for the bottles with the non-lytic media. However, for some of the microorganisms tested, an increase in TTD was observed for the bottles having the lytic media compared to the bottles with the non-lytic media. Since the sample size was small, these observations are not necessarily indicative of a substantial difference to TTD for bottles with non-lytic media compared with bottles with lytic media.

Figure 2A:
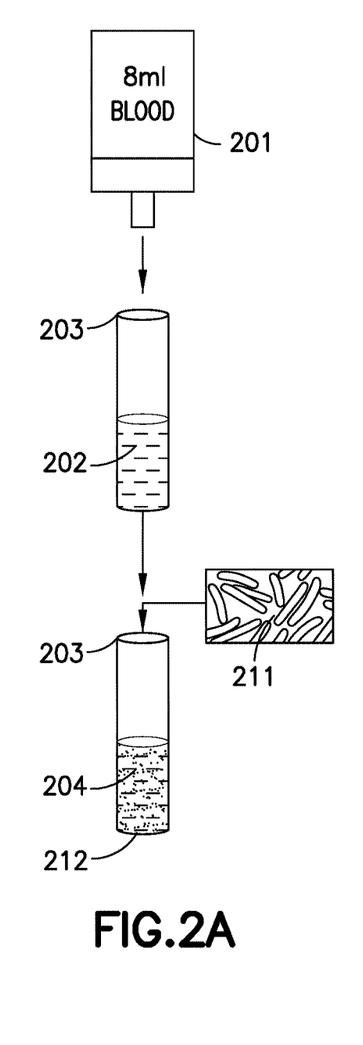
FIGS. 2A-C illustrate one embodiment of the present invention using a higher concentration of blood in broth to determine microorganism growth in the blood without the presence of an antibiotic inhibitor.
Figure 2B:
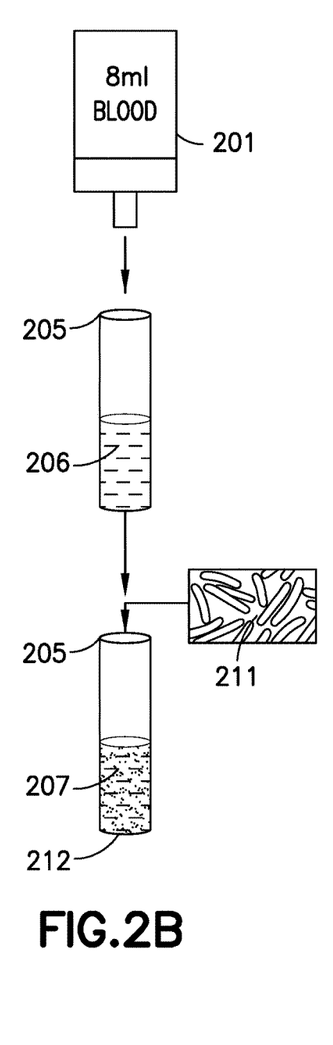
Figure 2C:
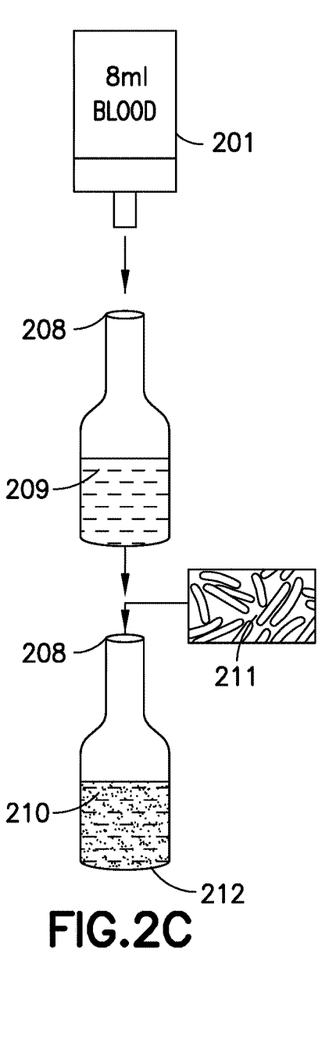

FIG. 2 illustrates the method of using a lower blood-to-broth ratio to determine microorganism growth in a blood sample without the presence of an antibiotic inhibitor. FIG. 2A illustrates 8 ml of blood 201 introduced into 4 ml of liquid media 202. The blood 201 and liquid media 202 are combined in a 16 ml sterilized and capped tube 203 creating a 2:1 blood-to-broth ratio 204. FIG. 2B illustrates 8 ml of blood 201 introduced into 8 ml of liquid media 206. The blood 201 and liquid media 206 are combined in a 19 ml sterilized and capped tube 205 creating a 1:1 blood-to-broth ratio 207. In FIG. 2A and FIG. 2B, the sensor in the container was a solid-state fluorescent $O_2$ sensor. The fluorescent signal changes were interpreted as an indication of microbial growth. FIG. 2C illustrates 8 ml of blood 201 introduced into 30 ml of liquid media 209. The blood 201 and liquid media 209 are combined in the commercially available BACTEC™ Standard Aerobic product ("StdAer") creating at least a 1:3 blood-to-broth ratio 210.

The liquid media is a modified media based on BACTEC Myco/F Lytic media with additional saponin. The samples are each loaded (i.e. spiked) with 10-100 CFU's of microorganisms 211. The microorganisms tested were *Alcaligenes faecalis, Candida albicans, Candida glabrata, Enterococcus faecalis, Escherichia coli, Neisseria meningitides, Pseudomonas aeruginosa, Staphylococcus aureus* (2 different strains), *Staphylococcus epidermidis, Streptococcus pneumonia*, and *Streptococcus pyogenes*. The sensors 212 used on the bottom of the tubes were made with the similar formulation as in BACTEC Myco/F Lytic bottles.

For each of the microorganisms, the blood culture bottles 203, 205, 208 were inverted 5 times immediately after the addition of the microorganisms 211 and then loaded into a BACTEC FX instrument. An adaptor was used to hold the tubes, so that the tubes stayed in the stations firmly and were located at the proper positions for detection. The tubes and bottles were incubated for 5 days and the signals from the culture bottle sensors 212 were detected for TTD analysis. Triplicate cultures were performed for each microorganism.

The results for the procedures are depicted in Table 2 below. As shown in Table 2, the blood culture bottles 203, 205 (FIG. 2) with blood-to-broth ratios of 1:1 207 and 2:1 204 showed similar or even shorter TTD as compared to the commercially available BACTEC™ Standard Aerobic bottles with at least a 1:3 blood-to-broth ratio.

TABLE 2

Comparison of low volume/low ratio TTD with TTD for standard 1:4 ratio

| Organisms | Blood to Broth 1:1 | Blood to Broth 2:1 | StdAer (Control) |
|---|---|---|---|
| Alcaligenes faecalis | 14.9 | 17.1 | 19.6 |
| Candida albicans | 20.3 | 22.7 | 22.6 |
| Enterococcus faecalis | 10.2 | 10.0 | 11.1 |
| Escherichia coli | 7.9 | 9.6 | 10.9 |
| Neisseria meningitidis | 12.7 | 18.2 | 19.1 |
| Pseudomonas aeruginosa | 11.4 | 12.4 | 15.4 |
| Staphylococcus aureus (strain #1) | 8.6 | 8.8 | 12.2 |
| Staphylococcus aureus (strain #2) | 8.5 | 9.0 | 11.9 |
| Streptococcus epdidermidis | 13.4 | 13.2 | 17.9 |
| Streptococcus pneumoniae | 12.2 | 12.8 | 14.0 |
| Streptococcuspyogenes (Strp. group A) | 8.7 | 9.0 | 10.8 |
| Average | 11.7 | 13.0 | 15.0 |
| (Standard Deviation) | (3.6) | (4.6) | (4.2) |

The average TTD of the 11 tested microorganisms in the preparations having the 1:1 blood-to-broth ratio 207 was 11.7 hours. The BACTEC Standard Aerobic bottles 208 with a more diluted blood-to-broth ratio of at least 1:3 210 had an average TTD of 15.0 hours, which was longer than the 1:1 sample 207. Similarly, the average TTD for the 16 ml bottle 210 with a 2:1 blood-to-broth ratio 204 was 13.0 hours. The shorter TTD for the 1:1 and 2:1 blood-to-broth ratios 207, 204 is an unexpected result and improvement over current more diluted blood-to-broth ratios like the BACTEC Standard Aerobic bottles with at least a 1:3 blood-to-broth ratio 210.

Example 2: Growth with Antibiotics in the Culture Media Inhibitor

Figure 3A:
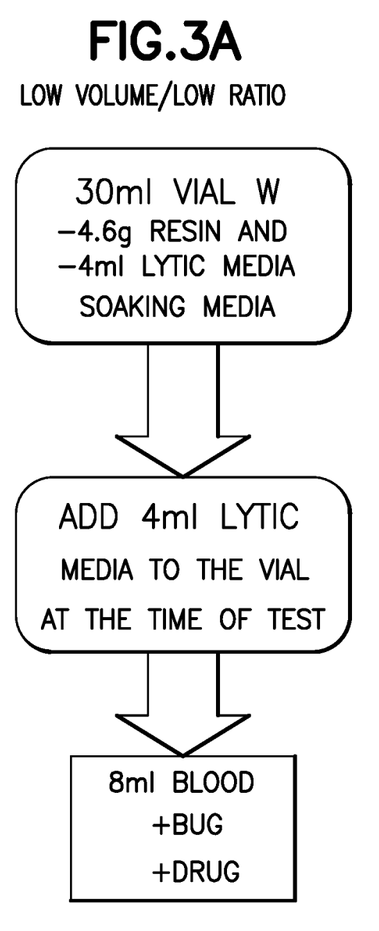
FIGS. 3A-C illustrate the method of using a higher concentration of blood in broth (providing a lower blood-to-broth ratio of 1:1) to determine microorganism growth in a blood sample that contains an antibiotic inhibitor.
Figure 3B:
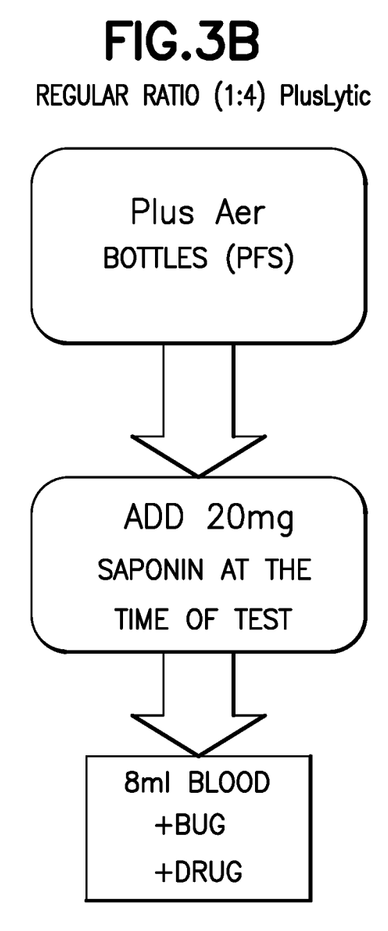
Figure 3C:
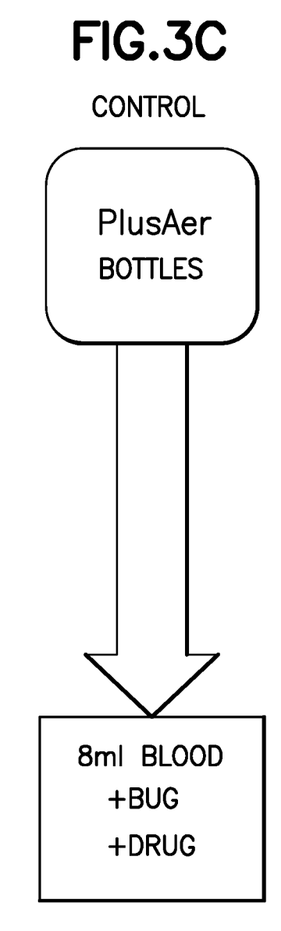

FIG. 3 illustrates the method of using a higher concentration of blood in broth (thereby providing a lower blood-to-broth ratio of 1:1) to determine microorganism growth in a blood sample that contains an antibiotic that would inhibit growth of at least some microorganisms. The TTD of microorganism growth in the presence of an antibiotic may be shortened in a sample that uses a resin in addition to growth media to enhance the growth of microorganisms. The primary function of the resin is to neutralize or adsorb antibiotics in patient blood. Resin can otherwise significantly reduce the inhibitory effect of antibiotics and make media volume reduction possible. It has also been suggested that lytic reagents in blood culture media are beneficial to microorganism recovery and shortened TTD. This is potentially due to blood cell lysis which in turn releases phagocytized microorganism and yield better recovery. One example of a commonly used lytic reagent shown to effectively lyse blood cells without affecting the viability and growth of microorganisms is saponin, a plant extract. In order to maximize the TTD of a microorganism growth, additional saponin may be added to mixtures having a higher concentration of blood in broth at the time of inoculation. The skilled person is aware of other lytic reagent and the present invention is not to be limited the use of any one lytic reagent.

The performance of 1:1 blood-to-broth ratio in the presence of an inhibitory antibiotic was tested in comparison to a standard diluted blood-to-broth ratio at least 1:3. Two different sample preparations for the 1:1 blood-to-broth ratio are described below.

FIG. 3A illustrates a low volume/low ratio preparation that is prepared in a 30 ml vial with the resin and lytic media disposed in separate chambers. The preparation contained resin and 8 ml total lytic media. The sensor in the container was a solid-state fluorescent 02 sensor. The fluorescent signal changes were used to determine microorganism growth. Low volume/low ratio preparations are sized to be combined with about 8 ml of blood sample wherein the blood to broth ratio is about 1:1. The low volume/low ratio preparation provided a 1:1 blood-to-broth ratio. The total 8 ml lytic media were separated into two parts. One part of the lytic media was in the 30 ml bottle with resin and the other part of the lytic media was in a separate device and the media therein was added under sterile conditions into the 30 ml bottle at the time the bottle was inoculated with both the blood sample and the microorganisms.

FIG. 3B illustrates the second sample preparation identified as "PlusLytic". The PlusLytic preparation uses the BACTEC Plus Aerobic product that is commercially available, which is 30 ml of media in the 80 ml bottle. At the time of testing, 8 ml of blood, a predetermined amount of antibiotic, 10-100 CFU's of microorganisms, and an additional 20 mg of saponin were combined with the 30 ml of media in the bottle. The ratio of blood to media is 8:30 which is about one part blood to 3.7 parts media. This ratio is typically referred to as 1:4 even though the volume of media is not quite 4 times the amount of sample.

The control test sample preparation is depicted in FIG. 3C and identified as "PlusAer". The PlusAer preparation uses the commercially available BACTEC Plus Aerobic product without any additional media components. At the time of testing, 8 ml of blood, a predetermined amount of antibiotic and 10-100 CFU's of microorganisms are combined with the contents of the BACTEC Plus Aerobic product. Therefore, the blood to broth ratio is a little less than 1:4 [i.e. 8 ml blood:30 ml media].

Each sample preparation was tested with 64 antibiotic/microorganism combinations. The antibiotics tested were Gentamicin, Amoxicillin-Clavulanate, Aztreonam, Ceftriaxone, Cefepime, Imipenem, Meropenem, Piperacillin-Tazobactam, Vancomycin, Tigecycline, Ciprofloxacin, Tetracycline, Fluconazole. The drug quantity inoculated into each test bottle was equivalent to the drug amount at its peak serum level in 7 ml of blood. These antibiotics were combined with certain microorganisms that they generally treat. For example, Amoxicillin-Clavulanate was combined with S. aureus, E. coli, and E. faecalis. Each sample was tested for both TTD and recovery of the microorganism in the presence of drugs.

The media was inoculated with blood sample, antibiotics and saponin a few minutes apart from each other.

In the TTD tests, the Low Volume/Low Ratio sample preparation had a similar performance to the control sample preparation, (the 1:4 PlusAer), for Ciprofloxicin, Piperacillin/Tazobactam, and Tigecycline. The Low Volume/Low Ratio preparation had a faster TTD as compared to the PlusAer preparation when tested with Vancomycin, Cefepime, Amoxicillin-Clavulanic Acid, Ceftriaxone, and Meropenem. See Table 3 below. The Low Volume/Low Ratio preparation had a slower TTD as compared to the PlusAer preparation for only one antibiotic, Gentamicin. The performance is surprising given the conventional view in the art that acceptable TTD cannot be achieved with higher amounts of blood relative to broth (i.e. lower ratios) (e.g. volume blood to volume media of 1:1 and 2:1) at low volumes (i.e. 20 ml or less total).

TABLE 3

Comparison of TTD/positivity for different combinations of Antibiotics and Microorganisms

| Antibiotic | Microorganism | Low Volume/low ratio TTD (hours) (approximate average) | Plus Lytic | Plus Aerobic |
|---|---|---|---|---|
| Vancomycin 280/µg | S. aureus | 23 | 15 | 18 |
| | S. aureus | 17.5 | 17.25 | 17 |
| | E. faecalis | 16 | 15.75 | 17 |
| | S. aureus | 18 | 15.25 | 18.75 |
| | E. faecalis | 20 | 18 | 19 |
| Amoxicillin/ clavulanic acid 81.2 µg | S. aureus | 65 | 25 | none |
| | E. coli | 10 | 10 | 10 |
| | E. faecalis | none | 40 | none |
| | E. coli | 10 | 10 | 10 |
| | S. aureus | 50 | 37.5 | none |
| Ceftriaxone 1050 µg | P. aeruginosa | none | none | none |
| | E. faecalis | 21 | 14 | 18 |
| | S. aureus | none | 42.5 | none |
| | P. aeruginosa | 19 | 15 | 18 |
| | S. aureus | 18 | 14 | 19 |
| Meropenem 343 µg | P. aeruginosa | 20 | 21 | 20 |
| | S. aureus | none | none | none |
| | E. faecalis | 51 | 34 | 49 |
| | P. aeruginosa | 35 | 39 | none |
| | E. faecalis | 16 | 14 | 12 |
| | P. aeruginosa | none | none | none |
| Cefepime 1351 µg | S. aureus | none | none | none |
| | E. faecalis | 23 | 21 | 29.5 |
| | S. aureus | none | none | none |
| | E. faecalis | 10 | 10 | 10 |
| | E. Coli | 11 | none | none |
| | E. faecalis | 13 | 12 | 13 |

With regard to drug absorption efficiency, the low volume low ratio preparation proved to have a faster absorption rate. The overall antibiotic absorption efficiency in a lower volume preparation is similar to that of the PlusAer preparation.

Figure 4A:
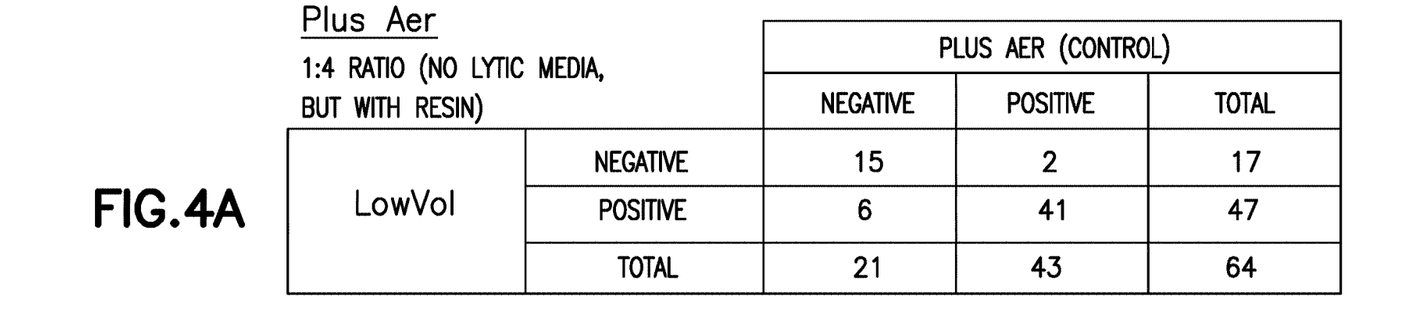
FIGS. 4A-C illustrate the recovery rate comparison between the PlusAer, PlusLytic and MicroVolume sample preparations in the presence of an antibiotic.
Figure 4B:
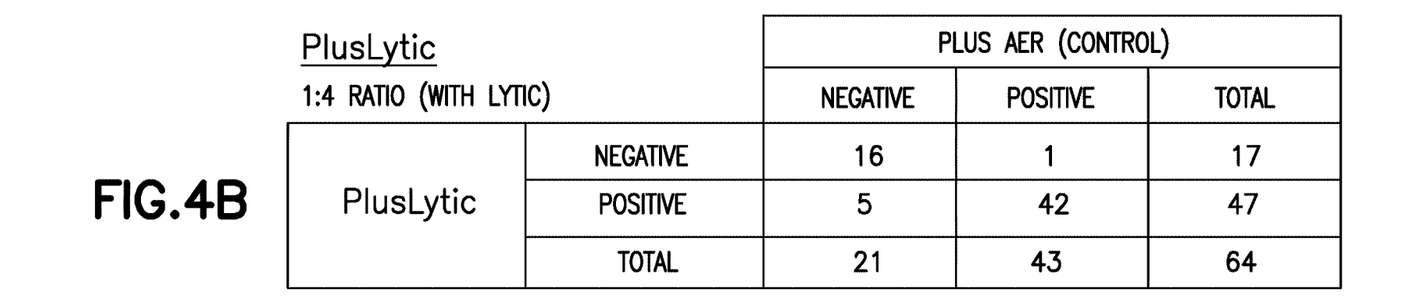
Figure 4C:
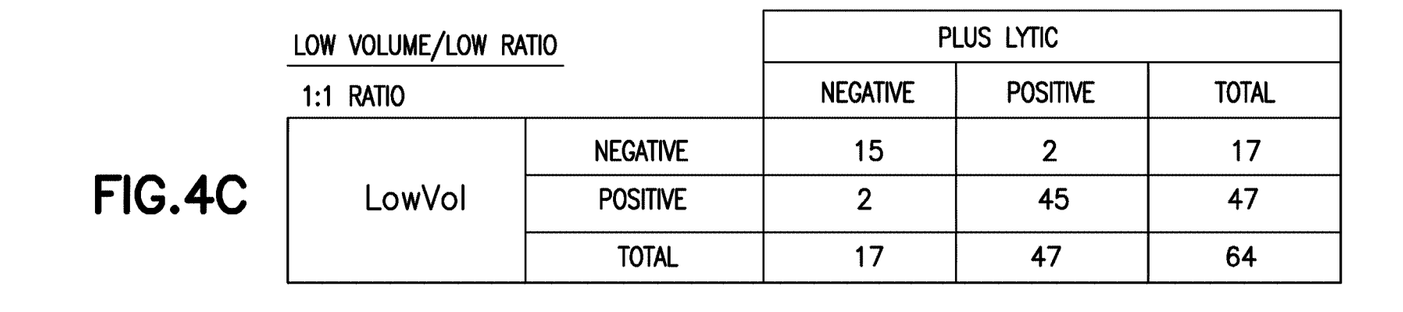

FIG. 4 compares the recovery rate of microorganisms among the PlusAer, PlusLytic and low volume/low ratio sample preparations in the presence of an antibiotic. In each comparison, the 64 antibiotic/microorganism combinations tested either positive or negative for microbial growth in the respective preparation.

FIG. 4A compares the recovery rate of the low volume/low ratio preparation containing a 1:1 blood to broth preparation with the control, which was the PlusAer preparation (which has a 1:4 ratio of blood to broth). The low volume/low ratio preparation tested positive in 47 instances, while the PlusAer control preparation tested positive in 43 instances. The PlusAer control preparation tested negative in 21 instances, while the low volume/low ratio preparation tested negative in 17 instances. Discrepant results can be shown in 2 instances where the low volume/low ratio preparation tested negative while the PlusAer tested positive for the same antibiotic/microorganism combination. Discrepant results were obtained in 6 instances where the PlusAer control preparation tested negative and the low volume/low ratio preparation tested positive for the same antibiotic/microorganism combination. The overall recovery performance of low volume/low ratio was statistically equivalent to PlusAer controls.

FIG. 4B compares the recovery rate of the PlusLytic preparation containing a 1:4 blood to broth ratio with the control, PlusAer preparation (also 1:4). The PlusLytic preparation tested positive in 47 instances, while the PlusAer control preparation tested positive in 43 instances. The PlusAer control preparation tested negative in 21 instances, while the PlusLytic preparation tested negative in 17 instances. Discrepant results can be shown in one instance where the PlusLytic preparation tested negative while the PlusAer tested positive for the same antibiotic/microorganism combination. Discrepant results are also shown in five instances where the PlusAer control preparation tested negative and the PlusLytic preparation tested positive for the same antibiotic/microorganism combination. Thus, the PlusAer (1:4) and Pluslytic (1:4) performed virtually identically when compared to the control.

FIG. 4C compares the recovery rate of the low volume/low ratio preparation containing a 1:1 ratio of blood to broth preparation with the PlusLytic preparation. The low volume/low ratio (1:1) preparation and Plus Lytic preparation both tested positive in 47 instances. The low volume/low ratio (1:1) preparation and the PlusLytic preparation both tested negative in 17 instances. Discrepant results can be shown in two instances where the low volume/low ratio (1:1) preparation tested negative while the PlusAer tested positive for the same antibiotic/microorganism combination. Discrepant results are also shown in two instances where the PlusAer control preparation tested negative and the low volume/low ratio (1:1) preparation tested positive for the same antibiotic/microorganism combination.

The recovery rate comparisons of FIGS. 4A and 4C indicate that the preparations containing a 1:1 blood to broth ratio show recovery rates that are about the same with the control than preparations with the 1:4 blood to broth ratio, namely the comparison of the low volume/low ratio preparation of FIG. 4A and the low volume/low ratio (1:1) preparation of FIG. 4C.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for culturing a blood sample, the method consisting of:

providing a consumable with a reservoir having a volume that does not exceed about 40 ml, the reservoir having a predetermined volume of a culture media disposed therein, wherein the predetermined volume of the culture media is selected so that, when a volume of blood is inoculated into the consumable, a ratio of the volume of blood to the volume of the culture media of about 1:1 will result;

inoculating the consumable with the volume of blood to provide a volume of inoculated culture media in an inoculated consumable, wherein the volume of blood is about 1 ml to about 3 ml, and wherein the ratio of the volume of blood to the volume of the culture media in the inoculated consumable is about 1:1 throughout the volume of inoculated culture media;

incubating the inoculated culture media to provide an incubated inoculated culture media, wherein the ratio of the volume of blood to the volume of the culture media and the ratio of blood volume to culture media volume in the incubated inoculated consumable is about 1:1 throughout the volume of the inoculated culture media;

detecting a signal from a sensor disposed in the incubated inoculated consumable, wherein the sensor is capable of detecting a change in the incubated inoculated consumable that occurs as a result of microbial growth therein, and wherein the ratio of the volume of blood to the volume of the culture media in the inoculated culture media in the incubated inoculated consumable remains about 1:1 in an entire volume of the inoculated culture media in the incubated inoculated consumable throughout the incubating and detecting steps; and determining, based on the detected signal, microorganism growth in the inoculated consumable.

2. The method of claim 1, wherein the culture media is a lytic media.

3. The method of claim 2, wherein the lytic media is about 0.25 grams of a lytic reagent for 100 ml of the culture media.

4. The method of claim 3, wherein the lytic reagent is saponin.

5. The method of claim 1, wherein the 1:1 blood to media ratio supports microorganism growth.

* * * * *